(12) United States Patent
Gobet et al.

(10) Patent No.: US 7,833,395 B2
(45) Date of Patent: Nov. 16, 2010

(54) ELECTRODE SYSTEM FOR AN ELECTROCHEMICAL SENSOR

(75) Inventors: Jean Gobet, Corcelles (CH); Philippe Niedermann, Peseux (CH); Philippe Rychen, Muespach-le-Haut (FR)

(73) Assignee: Adamant Technologies SA, La Chaux-de-Fonds (CH)

( * ) Notice: Subject to any disclaimer, the term of this patent is extended or adjusted under 35 U.S.C. 154(b) by 1125 days.

(21) Appl. No.: 10/586,668

(22) PCT Filed: Jan. 17, 2005

(86) PCT No.: PCT/CH2005/000019

§ 371 (c)(1),
(2), (4) Date: Jul. 20, 2006

(87) PCT Pub. No.: WO2005/071394

PCT Pub. Date: Aug. 4, 2005

(65) Prior Publication Data

US 2008/0257720 A1      Oct. 23, 2008

(30) Foreign Application Priority Data

Jan. 21, 2004    (EP) .................................. 04405039

(51) Int. Cl.
*G01N 27/30*    (2006.01)
*C25B 11/04*    (2006.01)

(52) U.S. Cl. ................ 204/292; 204/280; 204/284; 204/290.03

(58) Field of Classification Search .... 204/280–297.01; 216/13

See application file for complete search history.

(56) References Cited

U.S. PATENT DOCUMENTS

| | | | | |
|---|---|---|---|---|
| 4,062,750 A | * | 12/1977 | Butler | ........................ 257/253 |
| 4,874,500 A | * | 10/1989 | Madou et al. | ............... 204/412 |
| 5,512,489 A | | 4/1996 | Girault et al. | |
| 5,597,463 A | | 1/1997 | Birch et al. | |
| 5,810,725 A | * | 9/1998 | Sugihara et al. | ............. 600/372 |
| 2002/0149040 A1 | * | 10/2002 | Sun et al. | ..................... 257/295 |

FOREIGN PATENT DOCUMENTS

DE    41 31 731 A1    5/1993

(Continued)

OTHER PUBLICATIONS

Madore et al. (Environmental Sensing Potential with Arrays of Boron-Doped Diamond Microdisk Electrodes, 4th International Symposium on New Materials for Electrochemical Systems, Jul. 9-13, 2001, pp. 23-25).*

(Continued)

*Primary Examiner*—Alexa D Neckel
*Assistant Examiner*—Jennifer Dieterle
(74) *Attorney, Agent, or Firm*—Finnegan Henderson Farabow Garrett & Dunner LLP

(57) ABSTRACT

An electrode system for an electrochemical cell is provided, including a substrate, a measuring electrode connected to the substrate and formed from a number of electrically conducting and mutually connected microdisks, and a generating electrode formed from an electrically conducting sheet and having a diameter that is greater than that of the microdisks. In one implementation, the microdisks are provided in cavities in the substrate.

16 Claims, 2 Drawing Sheets

FOREIGN PATENT DOCUMENTS

| | | |
|---|---|---|
| EP | 0 569 908 B1 | 11/1993 |
| GB | 1 505 343 A | 3/1978 |
| WO | WO 90/12314 A1 | 10/1990 |
| WO | WO90/12314 * | 8/1996 |
| WO | WO 01/86276 A1 | 11/2001 |
| WO | WO 02/095387 A1 | 11/2002 |

OTHER PUBLICATIONS

PTO 96-4882, Micro multi electrode arrangement, translation of document WO90-12314.*

PCT International Search Report, for PCT/CH2005/000019, mailed Apr. 14, 2005 (3 pages).

European Search Report, for EP 04405039, dated Jun. 8, 2004 (3 pages).

Rychen, Ph. et al., "Environmental Sensing Potential with Arrays of Boron-Doped Diamond Microdisk Electrodes," 4$^{th}$ International Symposium on New Materials for Electrochemical Systems, Jul. 9-13, 2001, pp. 23-25.

Soh, K.L. et al., "CVD Diamond Anisotropic Film as Electrode for Electrochemical Sensing," Sensors and Actuators B, vol. 91, Jun. 1, 2003, pp. 39-45.

Ross, B. et al., "Ultramicroelectrode Arrays as Transducers for New Amperometric Oxygen Sensors," Sensors and Actuators B, vol. B07, No. 1/3, Mar. 1, 1992, pp. 758-762.

Written Opinion of the International Searching Authority, for PCT/CH2005/000019, (5 pages).

* cited by examiner

ELECTRODE SYSTEM FOR AN
ELECTROCHEMICAL SENSOR

This application is a national stage filing under 35 U.S.C. §371 of International Application No. PCT/CH2005/000019, filed on Jan. 17, 2005.

TECHNICAL FIELD

The present invention generally relates to electrochemical sensors intended for measuring the concentration of a chemical substance in a liquid, for example. Such devices find a particularly advantageous, but not exclusive, application in the detection of chlorine levels in drinking water or the water in swimming pools.

The invention relates more particularly to an electrode system for an electrochemical cell and to its manufacturing process.

BACKGROUND INFORMATION

Electrochemical sensors of the above-noted type necessarily comprise a measurement electrode, a reference electrode and a counterelectrode. Another type of such sensors is also known, which further includes what is called a generator electrode and its counterelectrode. The addition of these two latter electrodes, the effect of which is to modify the concentration of species present in solution, allows the environment of the measurement electrode to be locally controlled.

For example, the pH of the solution may be locally modified by applying a current to the generator electrode. A cathode current will result in the production of $OH^-$ ions (the pH then becoming more basic) and, conversely, an anode current will result in the production of $H^+$ ions (the pH then becoming more acid). A counterelectrode associated with the generator electrode, a counterelectrode associated with the measurement electrode (or working electrode) and a reference electrode are necessary in order to produce a complete sensor.

The latter electrodes, the dimensions of which need not be microscopic, are well known in the field in question and may be mounted separately. For example, U.S. Pat. No. 5,597,463 describes a sensor of this second type, which is intended to perform a titration and with which the measurement made is of the potentiostatic type.

It will be readily understood that it is particularly advantageous to use, as measurement electrode, electrodes of very small dimensions, not only because this allows the space between the measurement electrode and the generator electrode to be reduced, but also because the effects of the turbulence of the liquid in the cell are thereby minimized. Such electrodes of small dimensions are referred to without distinction in the rest of the description as either "microelectrodes" or "microdisks," the latter term being due to the fact that the microelectrodes are usually of circular shape.

Document WO 02/095387 describes a structure, shown in FIG. 1, using an electrically conducting substrate 10, advantageously made of doped silicon, the lower face of said substrate being covered with a metallization layer 11. Its upper face is covered with a passivation layer 12 formed from a multilayer comprising two sublayers, one of $SiO_2$ and the other of $Si_3N_4$, which multilayer is known to exhibit excellent stability in an aqueous medium.

The passivation layer 12 is pierced by a regular array of circular through-apertures housing a conducting microdisk 13 substantially thicker than the layer and extending slightly therebeyond so as to avoid any contact of the solution to be measured with the substrate.

The microdisks are formed from the desired electrode material(s), for example by a multilayer comprising titanium, platinum and gold layers. These layers together constitute the measurement electrode of the system.

Document WO 90/12314 proposes an arrangement of the same type, but in which the substrate is made of an inert material and the microelectrodes are constructed on the material by the deposition of successive layers. The contacts to these electrodes are produced through apertures made in the substrate.

SUMMARY OF THE INVENTION

An object of the present invention is to provide an improved measurement electrode structure, not only from the standpoint of its durability and its effectiveness, but also that of its production cost.

More precisely, embodiments of the invention relate to an electrode system intended for an electrochemical cell, the cell being of the type which comprises a substrate and, associated with it and close together, on the one hand, a measurement electrode formed from a plurality of electrically conducting microdisks connected together and, on the other hand, a generator electrode formed from an electrically conducting plate pierced by circular apertures larger in diameter than the microdisks and placed so that each aperture is concentric with a microdisk. In one embodiment, the system is characterized in that:

the substrate is made of an electrically conducting material and is pierced on its upper face, by a regular array of cavities of substantially cylindrical shape; and the microdisks forming the measurement electrode are contained within these cavities.

Electrode systems consistent with embodiments of the invention may also have one or more of the following features:

it may include an electrically insulating layer deposited on the substrate and pierced by a plurality of circular apertures that are centered on the cavities and have a smaller diameter than said cavities;

the microdisks may comprise a thin metallization, which is deposited on the bottom of each cavity and has substantially the same or smaller diameter as the apertures of the insulating layer, and, optionally, a thick metallization at least partly filling the rest of the cavity;

the thin metallization may comprise a multilayer formed from an adhesion layer and a diffusion barrier layer, which may be made of titanium and platinum respectively;

the thick metallization may be formed from the desired electrode material, which may be gold;

the thick metallization may either be flush with the upper face of the substrate or it may be covered with an active layer that is flush with the upper face of the substrate;

the generator electrode may either be a thin layer of conducting diamond or a thick conducting layer which forms, around the microelectrodes, a funnel-shaped rounded wall defining a confinement volume protecting them from the hydrodynamic flow of the solution to be treated; and/or the substrate may be made of silicon rendered conducting by doping.

Embodiments of the present invention also relate to a process for producing the measurement electrode of an electrode system as defined above. In accordance with one embodiment, the process comprises the following operations in succession:

a conducting substrate is provided;

the insulating layer is deposited on its upper face;

a mask provided with an array of circular apertures is formed on the insulating layer, the arrangement and the diameter of which apertures correspond to the array of microdisks to be produced;

the insulating layer is etched through the mask so as to obtain the circular apertures;

the substrate is deeply etched through these apertures so as to obtain the cavities;

the thin metallizations are deposited on the bottom of each cavity; and said thick metallizations are deposited on the thin metallizations.

Processes consistent with embodiments of the invention may also have one or more of the following features:

the insulating layer and the substrate may be etched by plasma etching or by wet chemical etching;

the thin metallizations may be deposited by vacuum evaporation; and/or the thick metallizations may be deposited by galvanic growth or by catalytic precipitation.

BRIEF DESCRIPTION OF THE DRAWINGS

Other features of the invention will become apparent from the following description, given with regard to the appended drawing in which.

DETAILED DESCRIPTION

Figure 1:
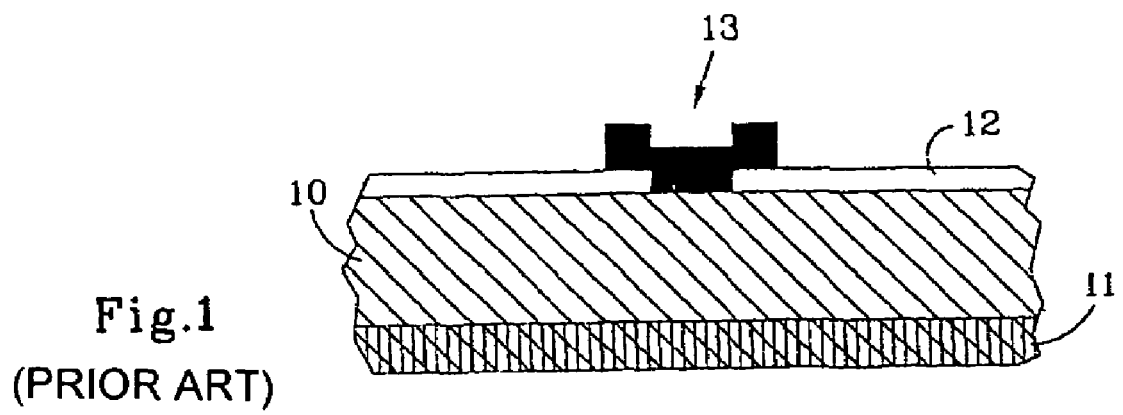
FIG. 1 is a cross-sectional view of a conventional structure.
Figure 3:
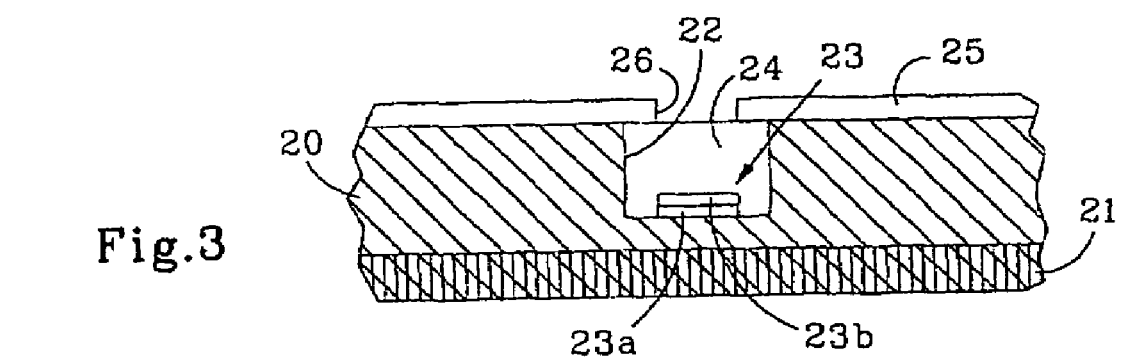
FIG. 3 is a sectional partial view on a large scale, along line M of FIG. 2, of this system.
Figure 2:
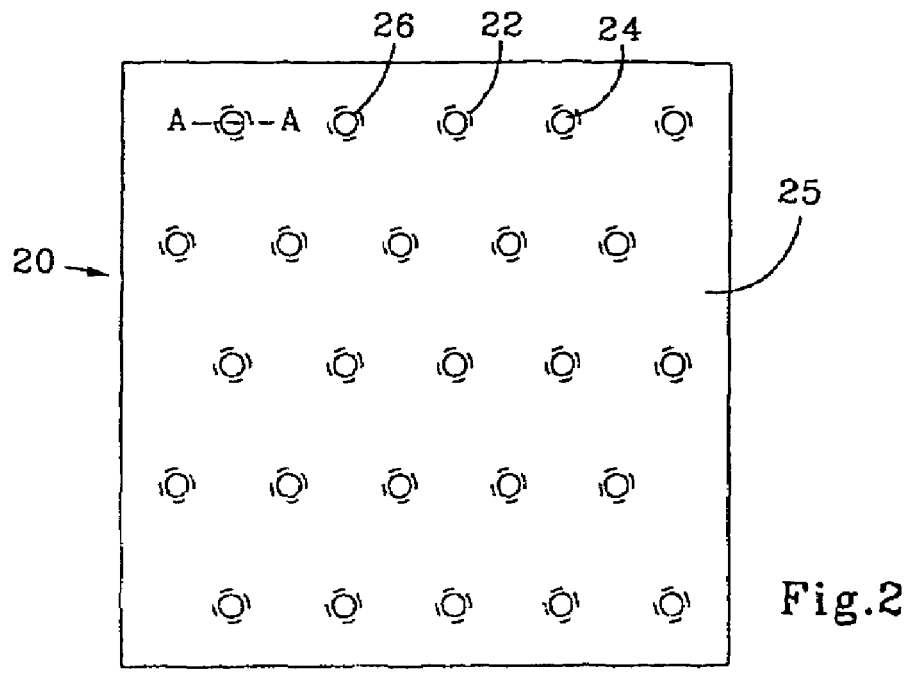
FIG. 2 is a plan view of an exemplary system, without its generator electrode, consistent with an embodiment of the invention.

The exemplary structure shown in FIG. 2 and FIG. 3 possesses an electrically conducting substrate 20 which is in the form of a square plate, typically with sides 2 to 10 mm in length and with a thickness of 0.5 mm. Advantageously, this plate is made of silicon rendered conducting by doping using techniques well known to those skilled in the art.

The lower face of the substrate 20 is covered with a conducting layer 21 made for example of titanium or aluminum, or formed from a multilayer comprising three sublayers, made of titanium, platinum and gold. The thickness of this layer 21 is about 0.2 to 0.3 µm.

The substrate 20 is pierced on its upper face by a regular array of approximately cylindrical cavities 22, the axes of which are perpendicular to the plane of the substrate. Typically, these cavities have a diameter of 2 to 20 µm and a depth of 2 to 20 µm and are spaced apart by about 40 to 400 µm.

The bottom of each cavity 22 is partially covered with a thin metallization 23 formed from an adhesion layer 23a and a conducting layer 23b resting on the adhesion layer. This multilayer for example made of titanium and platinum, has a thickness of about 0.2 to 0.3 µm. In some applications, the layer 23b also serves as a diffusion barrier. It should also be pointed out that the metallization 23 has a diameter 0.5 to 5 µm smaller than that of the cavity.

The set of metallizations 23 constitutes the measurement electrode of the system.

As a variant, the rest of the cavity 22 is filled with a thick metallization 24 formed from the desired electrode material, advantageously gold or any other material that can be deposited by galvanic growth, such as platinum, copper, etc.

In a variant (not shown), the gold deposit 24 only partly fills the cavity 22, the upper part of which then receives an active layer, for example made of Nafion or of an electropolymerized conducting polymer, such as Polypyrrole, constituting a selective, catalytic or protective membrane.

The upper face of the substrate 20 is covered with an insulating layer 25, called a passivation layer, which is formed for example from a multilayer comprising two sublayers of $SiO_2$ and $Si_3N_4$, and has a thickness of about 0.1 to 0.3 µm. This passivation layer is pierced by a regular array of circular through-apertures 26 that are centered on the cavities 22 and are of the same diameter as the thin metallizations 23, and therefore smaller in diameter than the cavities.

Figure 4:
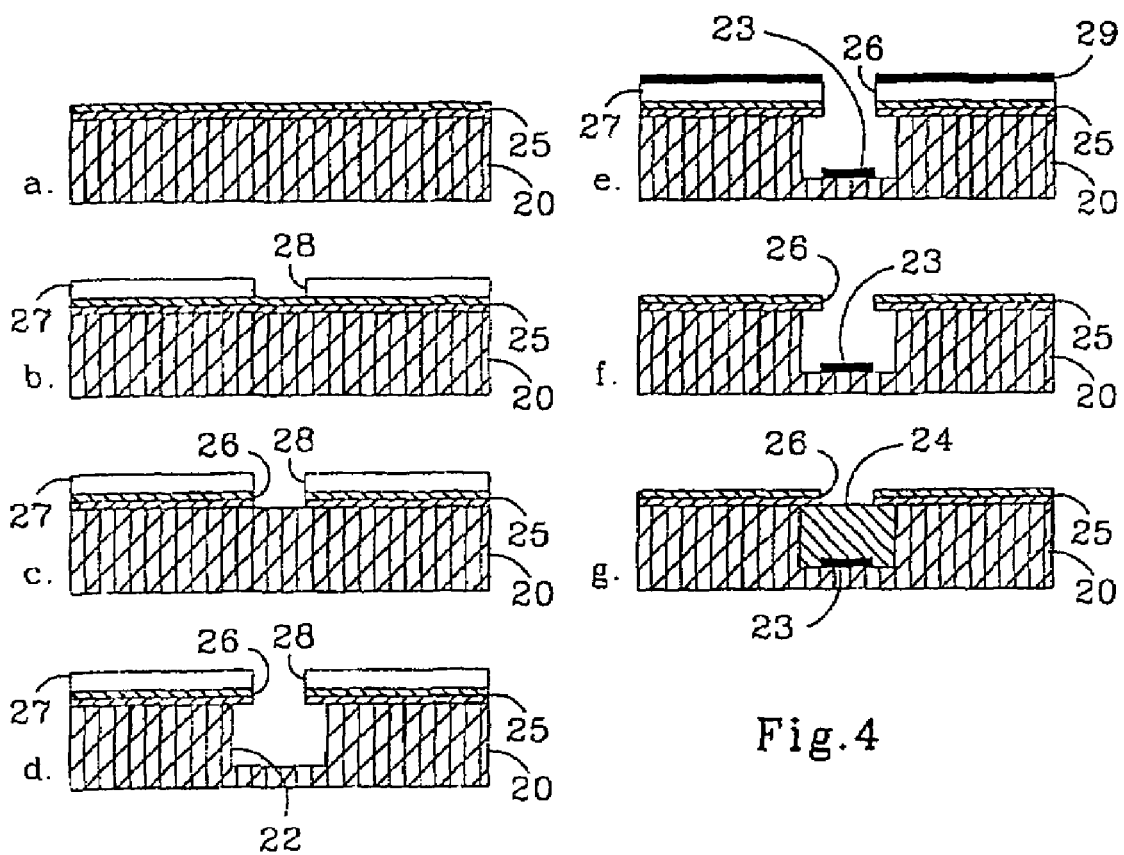
FIG. 4 illustrates exemplary operations for producing the structure shown in FIGS. 2 and 3, consistent with an embodiment of the invention.

FIG. 4 will now be described, which illustrates, by way of nonlimiting example, the main steps of an exemplary process for fabricating the structure shown in FIG. 2 and FIG. 3.

Step 1: FIG. 4a

The conducting silicon substrate 20 is covered with the passivation layer 25 by a thermal oxidation operation followed by a chemical vapor deposition, known to those skilled in the art by the name LPCVD.

Step 2: FIG. 4b

A photoresist mask 27 is formed on the passivation layer 25. The mask is provided with an array of circular apertures 28, the arrangement and the diameter of which correspond to the array of thin metallizations 23 to be produced.

Step 3: FIG. 4c

The passivation layer 25 is etched in a fluorine plasma so as to obtain the circular apertures 26.

Step 4: FIG. 4d

The cavities 22 are formed by deep plasma etching. The conditions under which this etching is carried out are such that the diameter of the cavities 22 is substantially greater than that of the apertures 26 of the passivation layer 25.

Step 5: FIG. 4e

The thin metallizations 23 that will form the measurement electrode of the system are deposited by vacuum evaporation. Thanks to the bridge that the photoresist layer 27 forms, the walls of the cavities 22 are not reached and the metallizations 23 have the same diameter as the apertures 26 of the passivation layer 25. Of course, this operation also metallizes the layer 27 with a layer 29.

Step 6: FIG. 4f

The metallization 29 and the photoresist layer 27 are removed using a solvent.

Step 7: FIG. 4g

Finally, a deposit of gold 24 is formed in the cavities 22 by galvanic growth.

Thus, a microelectrode system forming a measurement electrode is produced, which, compared with the structure of WO 02/095387, has the following main advantages:

the diameter of the electrodes may be greatly reduced, thereby correspondingly reducing the hydrodynamic dependence of the response of the sensor;

the cavity made in the substrate makes it possible for thick disks to be produced, without their diameter being correspondingly increased, thereby greatly extending their lifetime;

optionally, the cavity allows an active layer to be defined and anchored to the microelectrode;

only the upper face of the electrodes is exposed, thereby reducing their erosion; and simple operations are used to etch the passivation layer, in order to form the apertures 26, to etch the substrate, in order to form the cavities 22 and to remove both the metallization 29 and the photoresist 27. In particular, it should be pointed out that only a single mask (the photoresist mask 27) is needed to produce the cavities 22 and to form the microdisks 23 with precise dimensions.

Compared with the structure of document WO 90/12314, the exemplary system according to the invention has the advantage, since its substrate is conducting, of interconnecting the microelectrodes in parallel via their rear face, this having the effect of amplifying the output signal. Another appreciable advantage is that the cavities intended to receive the microelectrodes are produced directly in the substrate considerably more easily, and therefore less expensively.

In short, embodiments of the invention make it possible, by means of a simple and therefore inexpensive process, to obtain thick high-performance electrodes of precisely defined very small diameter.

The exemplary structure that has just been described may be supplemented with a metal generator electrode placed around the measurement electrodes, according to the teaching of document WO 02/095387.

However, with such a structure, it has been observed that the formation of a biofilm on the microelectrodes, and around them, consequently results in a progressive loss in sensitivity of the sensor.

Figure 5:
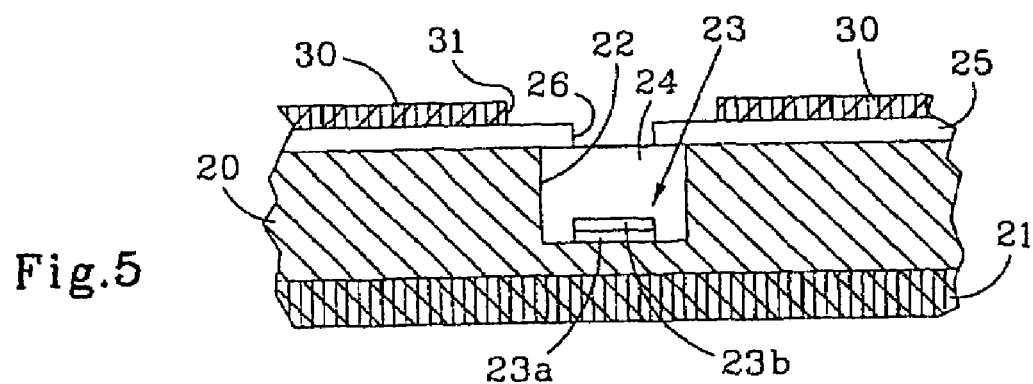
FIG. 5 and FIG. 6 illustrate two exemplary ways for producing a generator electrode, consistent with embodiments of the invention.

It is therefore also an object of the present invention to eliminate this contamination by replacing the metal generator electrode with a diamond generator electrode 30 deposited, as shown in FIG. 5, on the passivation layer 25.

The electrode 30 is formed from a thin layer of conducting diamond, which is pierced by circular apertures 31 of larger diameter than the microelectrodes 23 and placed so that each aperture 31 is concentric with a microelectrode. Typically, the electrode 30 has a thickness of 0.5 to 5 µm, while the circular apertures 31 have a diameter of 5 to 50 µm.

Tests carried out have confirmed that the diamond has the largest potential window in water and makes it possible to generate thereon highly oxidizing species, such as OH radicals, capable of effectively burning off organic matter.

Thus, a structure is proposed that prevents the formation of a contaminating biofilm affecting the sensitivity of the sensor. This effect is particularly appreciable when municipal waste water, very rich in organic matter, has to be treated.

Figure 6:
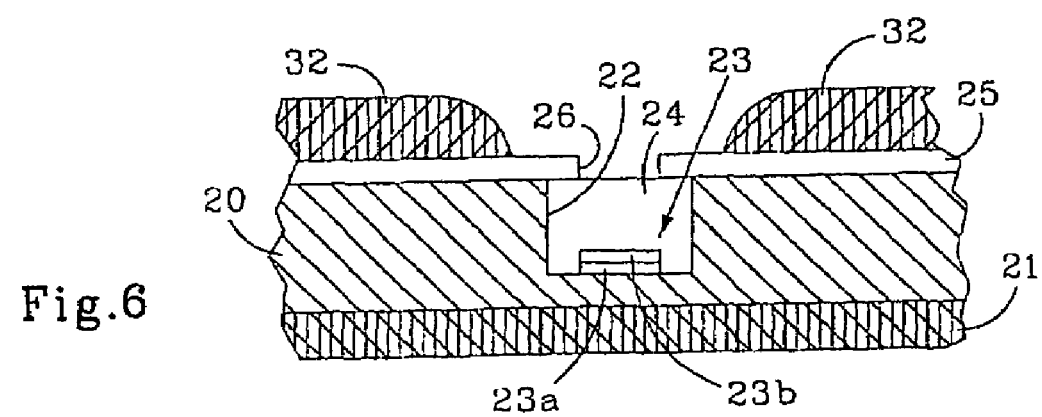

To conclude, referring again to FIG. 6, this shows the structure provided with a thick generator electrode 32 that forms, around the microelectrodes, a funnel-shaped rounded wall defining a confinement volume that protects said microelectrodes from the hydrodynamic flow of the solution to be treated.

This electrode 32 is advantageously made of gold and deposited by galvanic growth. Typically, its thickness is from 10 to 100 µm and the funnel that it forms has, at the base, a diameter of 10 to 50 µm.

Such a structure very greatly increases the effectiveness of the system, most particularly when stirred liquids or liquids flowing with a high flow rate have to be treated, since the space created around the microelectrodes not only allows the generated species to be concentrated but also offers a larger generator electrode area.

Finally, it should be noted that galvanic deposition of the thick electrode 32 is a simple and inexpensive operation.

The invention claimed is:

1. An electrode system for an electrochemical cell, comprising:
   a substrate formed of an electrically conducting material and pierced on at least one surface by a regular array of cavities, the regular array of cavities having a bottom in the substrate;
   a measurement electrode associated with the substrate, the measurement electrode being formed from a plurality of connected and electrically conducting microdisks that are contained within the cavities; and
   a generator electrode associated with the substrate, the generator electrode being formed from an electrically conducting plate pierced by circular apertures having a diameter that is larger than a diameter of the microdisks and placed so that at least one of the apertures is concentric with at least one of the microdisks.

2. The electrode system according to claim 1, wherein the generator electrode comprises conducting diamond.

3. The electrode system according to claim 1, wherein the generator electrode has a thickness allowing it to constitute, around and above the microdisks, a confinement volume protected from a hydrodynamic flow of a solution to be treated.

4. The electrode system according to claim 1, wherein the substrate comprises electrically conductive doped silicon.

5. The electrode system according to claim 1, further comprising an electrically insulating layer formed on the substrate and pierced by a plurality of circular apertures that are centered on the cavities and have a diameter that is smaller than a diameter of the cavities.

6. The electrode system according to claim 5, wherein the generator electrode comprises conducting diamond.

7. The electrode system according to claim 5, wherein the generator electrode has a thickness allowing it to constitute, around and above the microdisks, a confinement volume protected from a hydrodynamic flow of a solution to be treated.

8. The electrode system according to claim 5, wherein the microdisks further comprise a thin metallization formed on a bottom of each of the cavities, the thin metallization having substantially a same or smaller diameter as that of the apertures of the insulating layer, and further wherein the microdisks, optionally, include a thick metallization at least partly filling the rest of each of the cavities.

9. The electrode system according to claim 8, wherein the generator electrode comprises conducting diamond.

10. The electrode system according to claim 8, wherein the generator electrode has a thickness allowing it to constitute, around and above the microdisks, a confinement volume protected from a hydrodynamic flow of a solution to be treated.

11. The electrode system according to claim 8, wherein the thick metallization is flush with an upper face of the substrate.

12. The electrode system according to claim 8, wherein the thick metallization is covered with an active layer that is flush with an upper surface of the substrate.

13. The electrode system according to claim 8, wherein the thick metallization comprises an electroplatable material, such as gold, platinum, or copper.

14. The electrode system according to claim 8, wherein the thin metallization comprises a multilayer formed from an adhesion layer and a conducting layer.

15. The electrode system according to claim 14, wherein the adhesion layer comprises titanium and the conducting layer comprises platinum.

16. The electrode system according to claim 14, wherein the thick metallization comprises an electroplatable material, such as gold, platinum, or copper.

* * * * *